United States Patent [19]

Stahly

[11] Patent Number: 4,994,596

[45] Date of Patent: Feb. 19, 1991

[54] CYANOALKENYLATION PROCESS

[75] Inventor: Barbara C. Stahly, Baton Rouge, La.

[73] Assignee: Ethyl Corporation, Richmond, Va.

[21] Appl. No.: 471,614

[22] Filed: Jan. 29, 1990

[51] Int. Cl.$^5$ .................... C07C 253/08; C07C 253/10
[52] U.S. Cl. .................................... 558/332; 558/351; 558/352
[58] Field of Search ........................ 558/332, 351, 352

[56] References Cited

U.S. PATENT DOCUMENTS 3,228,831  1/1966  Nicholson et al. .................. 514/568
4,536,343  8/1985  Ramachandran .................... 558/351
4,581,176  8/1986  Davidson ............................. 558/341

OTHER PUBLICATIONS

Noller, "Chemistry of Organic Compounds," 3rd Ed., (1965), p. 585, W. B. Saunders Co., Phila. & London.

Primary Examiner—Joseph Paul Brust
Attorney, Agent, or Firm—Patricia J. Hogan; Richard J. Hammond

[57] ABSTRACT

1-Cyano-1-(4-alkylphenyl)alkenes having utility as chemical intermediates, especially in the preparation of ibuprofen and related pharmaceuticals, are prepared by reacting an alkylbenzene with an alkali metal cyanide and an acid halide in the presence of aluminum chloride.

8 Claims, No Drawings

CYANOALKENYLATION PROCESS

FIELD OF INVENTION

This invention relates to 1-cyano-1-(4-alkylphenyl)alkenes and more particularly to a process for preparing them.

BACKGROUND

As disclosed in U.S. Pat. Nos. 4,536,343 (Ramachandran) and 4,581,176 (Davidson), it is known that α-arylacrylonitriles are useful as chemical intermediates and that they can be prepared by reacting a suitable aryl ketone with an alkali metal cyanide and aluminum chloride, preferably in the presence of an activating amount of water and/or HCl. One of the ketones taught to be useful in the processes of Ramachandran and Davidson is 4-isobutylacetophenone, a compound which U.S. Pat. No. 3,228,831 (Nicholson et al.) teaches to be synthesizable by the reaction of isobutylbenzene with acetyl chloride.

When 4-isobutylacetophenone or an analogous ketone is subjected to a reaction of Ramachandran or Davidson, the product is a 1-cyano-1-(4-alkylphenyl)alkene. It would be desirable to be able to prepare such products directly from the appropriate alkylbenzenes to obviate the need for two separate reactions, i.e., the synthesis of the ketone and its subsequent conversion to a 1-cyano-1-(4-alkylphenyl)alkene.

SUMMARY OF INVENTION

An object of this invention is to provide a novel process for preparing 1-cyano-1-(4-alkylphenyl)alkenes.

Another object is to provide such a process utilizing an alkylbenzene as a reactant.

These and other objects are attained by reacting an alkylbenzene with an alkali metal cyanide and an acid halide in the presence of aluminum chloride.

DETAILED DESCRIPTION

Although alkylbenzenes in general are useful as reactants in the practice of the invention, those of greatest interest are the alkylbenzenes wherein the alkyl group contains 1-6 carbons. Such compounds include, e.g., the methyl-, ethyl-, propyl-, isopropyl-, butyl-, isobutyl-, pentyl-, and hexylbenzenes. Because of its utility in preparing an ibuprofen intermediate by the present process, the preferred alkylbenzene is ordinarily isobutylbenzene.

The alkali metal cyanide utilized may be lithium, sodium, potassium, rubidium, or cesium cyanide, but it is preferably the sodium or potassium cyanide, most preferably sodium cyanide. To produce good yields of the desired product, it is generally desirable to employ abut 1-5, preferably about 1-2 mols of the cyanide per mol of the alkylbenzene.

The acid halide reactant is ordinarily an alkanoyl halide containing 2-6 carbons, i.e., a compound corresponding to the formula RCOX, in which R is an alkyl group of 1-5 carbons and X is fluoro, chloro, bromo, or iodo. Exemplary of such compounds are acetyl chloride, acetyl fluoride, propanoyl chloride, butanoyl chloride, butanoyl bromide, pentanoyl chloride, and hexanoyl chloride. The chlorides are preferred, especially acetyl chloride. The acid halide and alkylbenzene are usually employed in substantially equimolar amounts, although either may be used in excess.

The amount of aluminum chloride used is generally about 1.0–1.5, preferably about 1.0–1.1 mols per mol of the alkyl benzene.

It is sometimes desirable to conduct the reaction in the presence of water and/or concentrated HCl as an activator which appears to effect an activation of one or more of the reactants and increase yields. The particular amount of water and/or HCl employed is an activating amount, i.e., an amount insufficient to hydrolyze the aluminum chloride completely, and may be provided simply by water naturally present in one or more of the other ingredients of the reaction mixture. When it is desired to employ additional water and/or HCl, the added amount is generally in the range of about 0.1–1.0 per mol of the alkylbenzene.

The reaction is suitably conducted in a solvent, which may be any solvent in which the reactants are soluble, such as an aliphatic or aromatic hydrocarbon (e.g., toluene, xylene, heptane, etc.), chlorobenzene, nitrobenzene, or the like.

In the practice of the invention, the ingredients of the reaction mixture may be combined in any suitable manner and heated at a suitable temperature, e.g., about 60°–120° C., preferably about 90°–100° C., to produce the desired product, a 1-cyano-1-(4-alkylphenyl)alkene. The time required to obtain good yields varies with the temperature but is frequently in the range of about 4–10 hours. A preferred manner of combining the ingredients is to prestir the alkali metal cyanide, aluminum chloride, and a solvent until a reaction between the cyanide and aluminum chloride has been accomplished before adding the remaining ingredients.

After completion of the reaction, the product can be recovered by conventional means or, alternatively, can be subjected to further reactions without being isolated when the further reactions would not be inhibited by impurities in the crude product. It is frequently desirable to subject the 1-cyano-1-(4-alkylphenyl)alkene to subsequent reactions, e.g., hydrogenation and/or hydrolysis. For example, 1-cyano-1-(4-isobutylphenyl)ethene can be hydrogenated by conventional means, e.g., in the presence of a palladium-on-carbon catalyst, and then hydrolyzed by conventional means, e.g., in the presence of acetic and sulfuric acids, to form ibuprofen, a useful pharmaceutical; and the other 1-cyano-1-(4-alkylphenyl)alkenes can be similarly treated to form analogous pharmaceuticals.

An advantage of the invention is its streamlining of the known process for preparing the desired products by first reacting an alkylbenzene with an acid halide to form a ketone and then converting the ketone to a 1-cyano-1-(4-alkylphenyl)alkene.

The following example is given to illustrate the invention and is not intended as a limitation thereof.

EXAMPLE

A mixture of 1.1 mL of 1.0 M aluminum chloride in nitrobenzene (1.1 mmol) and 100 mg (2.0 mmol) of finely-ground sodium cyanide was stirred at room temperature and treated with 73 microliters (1.0 mmol) of acetyl chloride, 450 mg of activated 3A molecular sieves, and 160 microliters (1.0 mmol) of 98% isobutylbenzene. After the reaction mixture had been heated at 100° C. for two hours, GC analysis showed 25 area % of 1-cyano-1-(4-isobutylphenyl)ethene.

It is obvious that many variations may be made in the products and processes set forth above without departing from the spirit and scope of this invention.

What is claimed is:

1. A process which comprises reacting an alkylbenzene wherein the alkyl group contains 1–6 carbon atoms with an alkali metal cyanide and an alkenoyl halide containing 1–6 carbon atoms in the presence of an effective amount of aluminum chloride for a time and at a temperature sufficient to form a 1-cyano-1-(4-alkylphenyl)alkene.

2. The process of claim 1 wherein the alkylbenzene is isobutylbenzene.

3. The process of claim 1 wherein the alkali metal cyanide is sodium cyanide.

4. The process of claim 1 wherein the alkanoyl halide is acetyl chloride.

5. The process of claim 1 wherein the reaction is conducted in a solvent.

6. The process of claim 1 wherein the solvent is nitrobenzene.

7. The process of claim 1 wherein the reaction is conducted in the presence of an activating amount of water and/or HCl.

8. A process which comprises reacting isobutylbenzene with sodium cyanide and acetyl chloride in the presence of aluminum chloride at a temperature of about 60°–120° C. to form 1-cyano-1-(4-isobutylphenyl)ethene.

* * * * *